United States Patent
Scommegna et al.

(10) Patent No.: US 8,328,556 B2
(45) Date of Patent: Dec. 11, 2012

(54) DENTAL IMPLANT

(75) Inventors: Gabriele Scommegna, Tavarnuzze Impruneta (IT); Maurizio Dolfi, Florence (IT)

(73) Assignee: Leone S.p.A., Sesto Fiorentino (Firenze) (IT)

( * ) Notice: Subject to any disclaimer, the term of this patent is extended or adjusted under 35 U.S.C. 154(b) by 1077 days.

(21) Appl. No.: 11/007,818

(22) Filed: Dec. 8, 2004

(65) Prior Publication Data
US 2006/0121417 A1 Jun. 8, 2006

(30) Foreign Application Priority Data
Jan. 19, 2004 (IT) .................... FI2004A0013

(51) Int. Cl.
*A61C 13/12* (2006.01)
*A61C 13/225* (2006.01)
*A61C 8/00* (2006.01)

(52) U.S. Cl. .................... 433/174; 433/172; 433/173
(58) Field of Classification Search .......... 433/172–176, 433/180, 182, 201.1; 606/301–331
See application file for complete search history.

(56) References Cited

U.S. PATENT DOCUMENTS

| | | | |
|---|---|---|---|
| 4,854,872 A * | 8/1989 | Detsch | 433/173 |
| 5,030,095 A * | 7/1991 | Niznick | 433/173 |
| 5,116,225 A * | 5/1992 | Riera | 433/173 |
| 5,195,891 A * | 3/1993 | Sulc | 433/173 |
| 5,197,881 A * | 3/1993 | Chalifoux | 433/173 |
| 5,316,477 A * | 5/1994 | Calderon | 433/173 |
| 5,350,301 A * | 9/1994 | De Buck | 433/173 |
| 5,417,570 A * | 5/1995 | Zuest et al. | 433/177 |
| 5,571,015 A * | 11/1996 | Siegmund | 433/173 |
| 6,068,480 A * | 5/2000 | Misch et al. | 433/173 |
| 6,217,331 B1 * | 4/2001 | Rogers et al. | 433/173 |
| 6,254,387 B1 * | 7/2001 | Bergstrom et al. | 433/49 |
| 6,283,753 B1 * | 9/2001 | Willoughby | 433/172 |
| 6,402,515 B1 * | 6/2002 | Palti et al. | 433/174 |
| 6,419,492 B1 | 7/2002 | Schroering | |
| 6,572,373 B2 * | 6/2003 | Tramonte | 433/173 |
| 2002/0031748 A1 * | 3/2002 | Crudo | 433/173 |
| 2003/0068599 A1 * | 4/2003 | Balfour et al. | 433/173 |
| 2003/0082498 A1 * | 5/2003 | Halldin et al. | 433/173 |
| 2003/0194679 A1 * | 10/2003 | Odrich et al. | 433/173 |

FOREIGN PATENT DOCUMENTS
WO  WO 96/26685  9/1996

* cited by examiner

*Primary Examiner* — Yogesh Patel
(74) *Attorney, Agent, or Firm* — McGlew and Tuttle, P.C.

(57) ABSTRACT

An abutment (2) connects with a fixture (1) by a Morse-taper type coupling, with the installation of a truncated-cone shank (21) of the abutment (2) into a corresponding cavity (11) exhibited by the fixture (1). The abutment (2) is provided with an appendix having a polygonal cross-section (22), and is positioned below the shank (21). The appendix is fitted into a corresponding impression (12) provided in the bottom of the cavity (11) of fixture (1). The abutment is also provided, on the side opposite to the appendix (22), with respect to the shank (21), with a portion (20, 24) intended for supporting a dental prosthesis (D). The appendix (22) can be rotated about its longitudinal axis, relative to the shank (21) of the abutment (2).

22 Claims, 11 Drawing Sheets

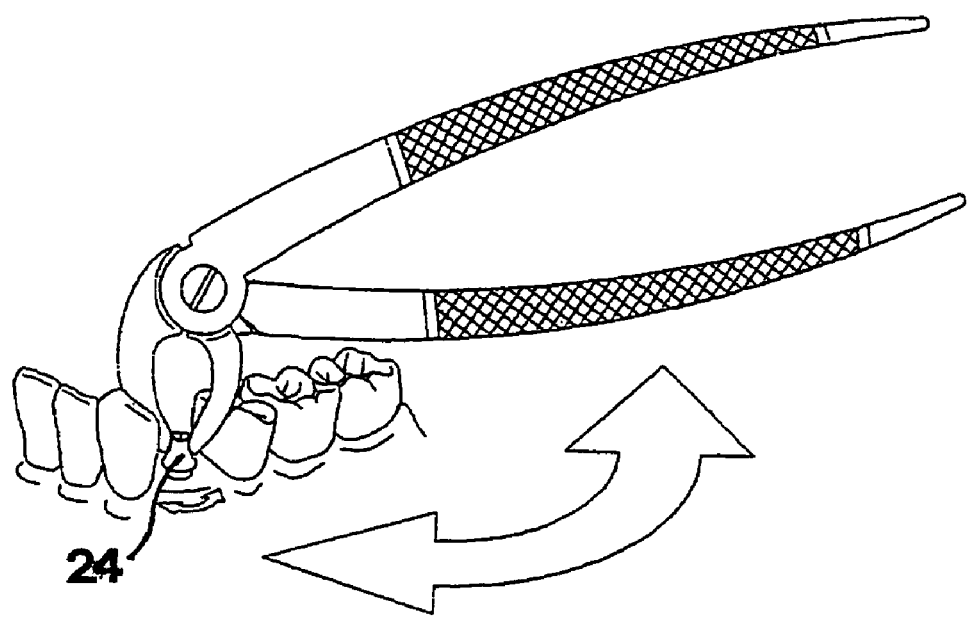
Fig. 16A
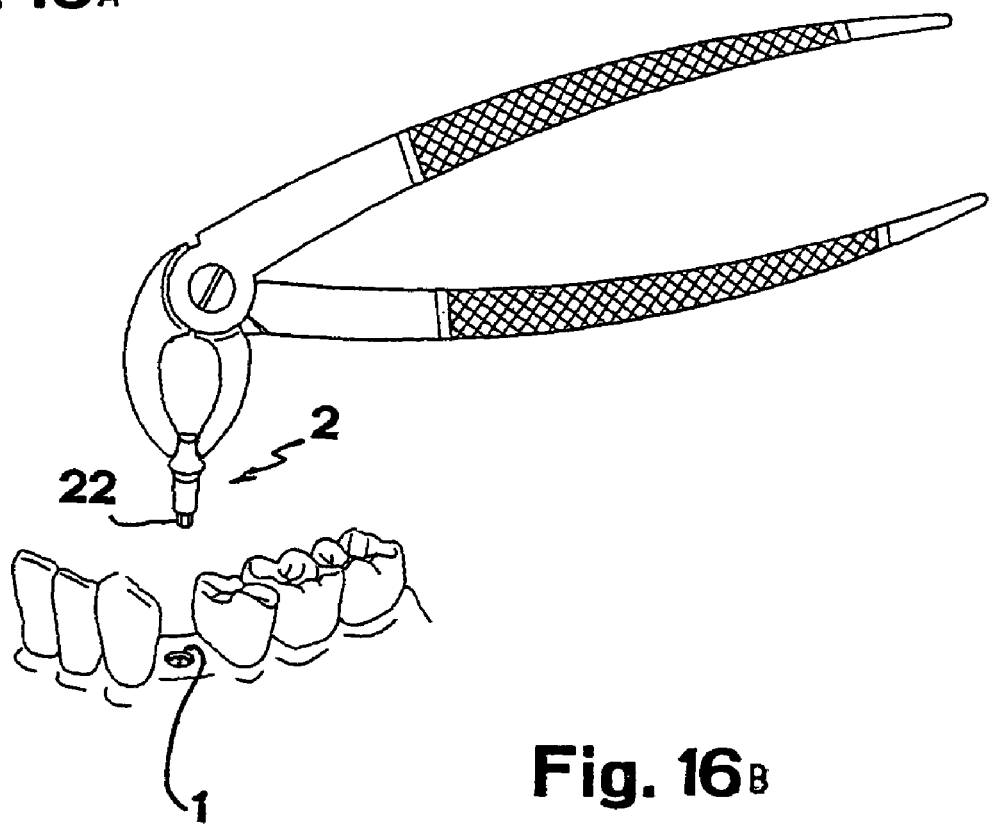
Fig. 16B

US 8,328,556 B2

DENTAL IMPLANT

FIELD OF THE INVENTION

The present invention relates to a dental implant.

BACKGROUND OF THE INVENTION

A dental implant is known to make up for the loss of one or more dental element, and to consist of one or more components intended to restore both the masticatory function and the aesthetic aspect.

In general, a dental implant comprises an artificial root or fixture to be implanted surgically in the bony tissue, and a stump or abutment intended for supporting a dental prosthesis and connected to the fixture. The abutment is connected to the fixture after a preset time allowing the correct execution of an osteo-integration process by which the fixture results afterwards integrated in the bony tissue. The fixture is generally provided with an outer threading to allow it to be screwed into the bony tissue, but it can also be shaped in a different way in order to be inserted by pressure into the implant seat.

More particularly, dental implants are known in which a coupling of Morse-taper coupling is made between the fixture and the abutment: the latter exhibiting a truncated-cone shank to be forced into a corresponding installation cavity formed in the fixture. To prevent the abutment to rotate relative to the fixture, the abutment's shank may be provided with an axial appendix of polygonal cross-section to be inserted into a corresponding impression provided in the bottom of the inner cavity of the fixture which receives the abutment. The presence of said appendix makes it also possible to establish a precise positional reference of the abutment with respect to the fixture. A dental implant thus structured is disclosed in the document WO 96/26685.

The Morse-taper coupling between the two parts of the implant, that is, fixture and abutment, is activated by axial impulsive forces exerted on the abutment by means of a suitable tool. Morse tapers are known to have a taper ratio of the tapered shank and the tapered cavity substantially in the range of 19.002:1 through 20.047:1. To disconnect the two parts it is necessary to apply either an impulsive force, of an intensity equal to that for the coupling, or a static tensile force of quite greater intensity. But, since the resistance of the Morse-taper coupling to the torsional loads is decidedly lower, the dentist—in most of the cases, when it is necessary to remove the abutment for intervening on the prosthesis or modifying the therapeutic program, prefers to resort to a maneuver for rotating the abutment which, once releases from the Morse-taper coupling, can be easily extracted. However, when the abutment is of a type provided with the above said appendix having polygonal cross-section, the rotational maneuver above mentioned is in actual fact prevented, since the appendix in question is inserted into the respective seat, correspondingly shaped with polygonal cross-section, exhibited by the fixture. On the other hand, when the abutment is not provided with an appendix of polygonal cross-section type, there is no accurate reference for the position of the abutment, with respect to the fixture, during both the preparation of the prosthesis and the fitting tests of the implant on the patient.

SUMMARY OF INVENTION

One object of the present invention is to propose a dental implant able to ease the disconnection of the abutment from the fixture, thereby avoiding the application of impulsive forces.

A further object of the present invention is to propose a dental implant which allows maintaining a precise reference for the position of the abutment relative to the fixture.

This result has been achieved, according to the invention, by adopting the idea of making a dental implant having the characteristics indicated in the claim 1. Further characteristics being set forth in the dependent claims.

The present invention makes it possible to make a dental implant with self-blocking/self-locking Morse-taper coupling which, therefore, allows reducing the gap between the coupled surfaces of the abutment and fixture to a minimum, while maintaining or restoring all the time also the correct mutual orientation of these two elements and facilitating the disconnection thereof even after a prolonged period of permanent coupling. Moreover, a dental implant according to the present invention is relatively easy to make and reliable even after a long service period.

These and other advantages and characteristics of the invention will be best understood by anyone skilled in the art from a reading of the following description in conjunction with the attached drawings given as a practical exemplification of the invention, but not to be considered in a limitative sense.

BRIEF DESCRIPTION OF THE DRAWINGS

FIGS. 16A and 16B show schematically the unseating of an abutment.

DETAILED DESCRIPTION OF THE INVENTION

Figures 1A, 1B:
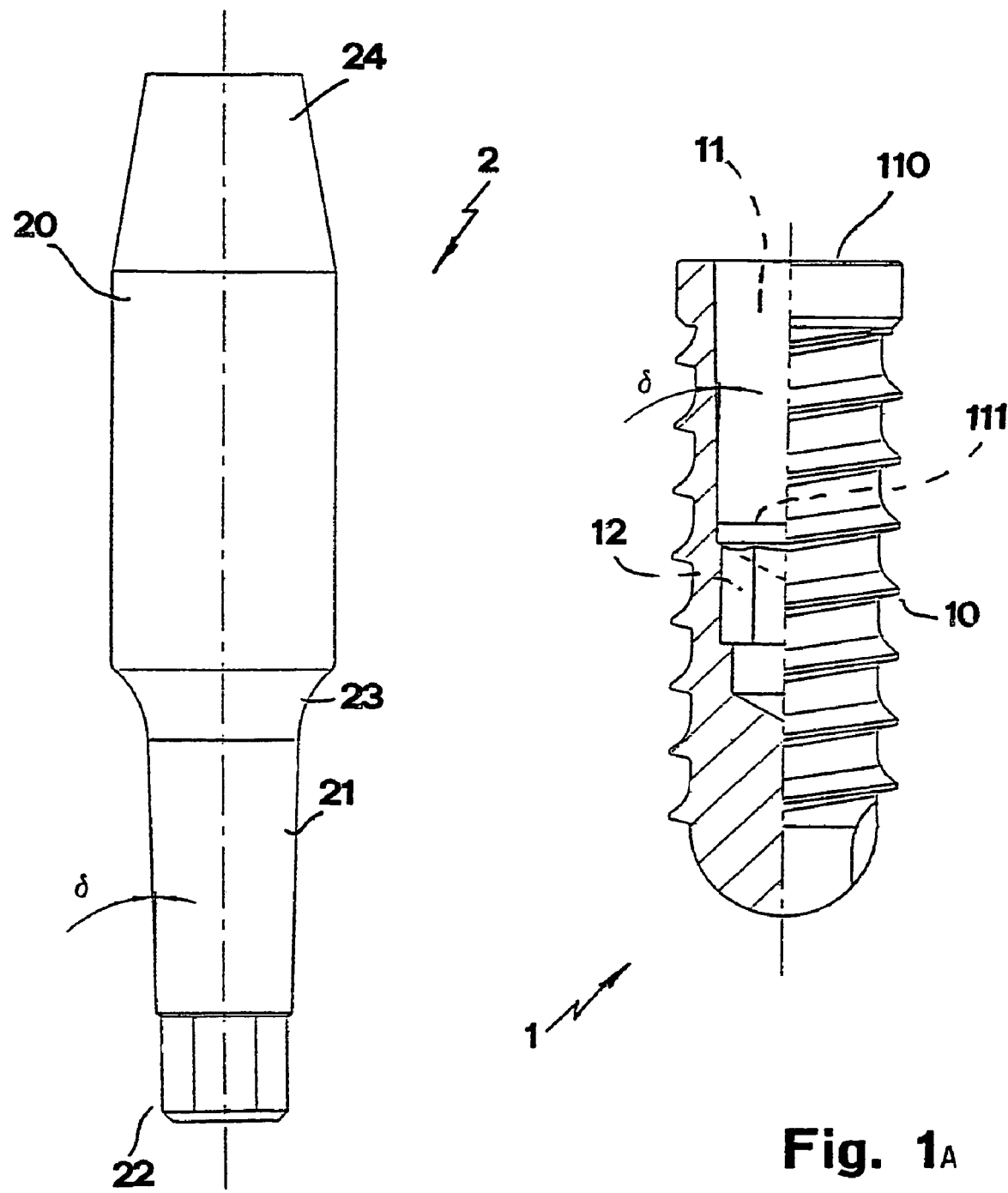
FIG. 1A is a schematic side view, in partial longitudinal section, of a fixture for dental implants according to the invention.
FIG. 1B is a schematic side view of an abutment for dental implants according to the invention.

Reduced to its basic structure, and reference being made to the figures of the attached drawings, a dental implant according to the present invention is of a type comprising an artificial root or fixture (1) and a stump or abutment (2).

The fixture (1) is to be implanted in the subgingival bony tissue (3) in correspondence of a missing tooth. According to the example shown in the drawings, the said fixture (1) comprises a body with external threading (10), an internal cavity (11) and a seat (12) with polygonal cross-section—for example, hexagonal—on the bottom of said cavity (11). The latter has a truncated-cone development, with the major base (110) up and the minor base (111) down. The half angle (6) of the cone has a preset value, for example, a nominal value of 1.5°.

According to the exemplary embodiments shown in the attached drawings, the said abutment (2) comprises a body with an upper, or coronal, part (20) terminating with a substantially truncated-cone face (24), intended for supporting the dental prosthesis (D), and with a truncated-cone shank (21) provided with an appendix (22) having polygonal cross-section, that is, of a shape corresponding to that of the seat (12) with polygonal cross-section of fixture (1).

Figures 3, 4:
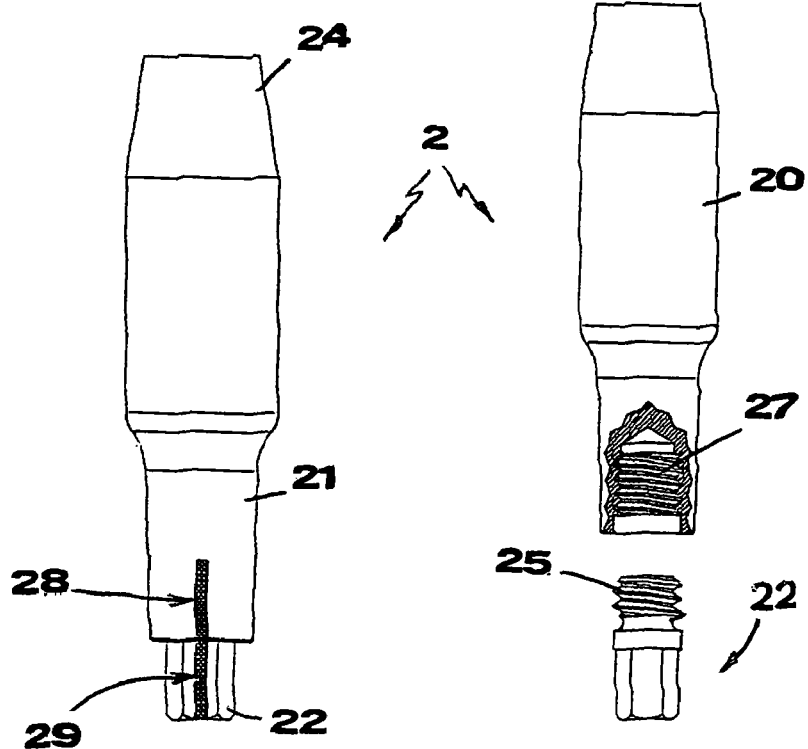
FIG. 3 is a further side view of the abutment of FIG. 2, showing two positional references provided on the polygonal cross-section appendix and, respectively, on the truncated-cone shank of the abutment.
FIG. 4 is a schematic exploded view, in partial longitudinal section, of the abutment shown in FIGS. 2 and 3.
Figures 5, 6:
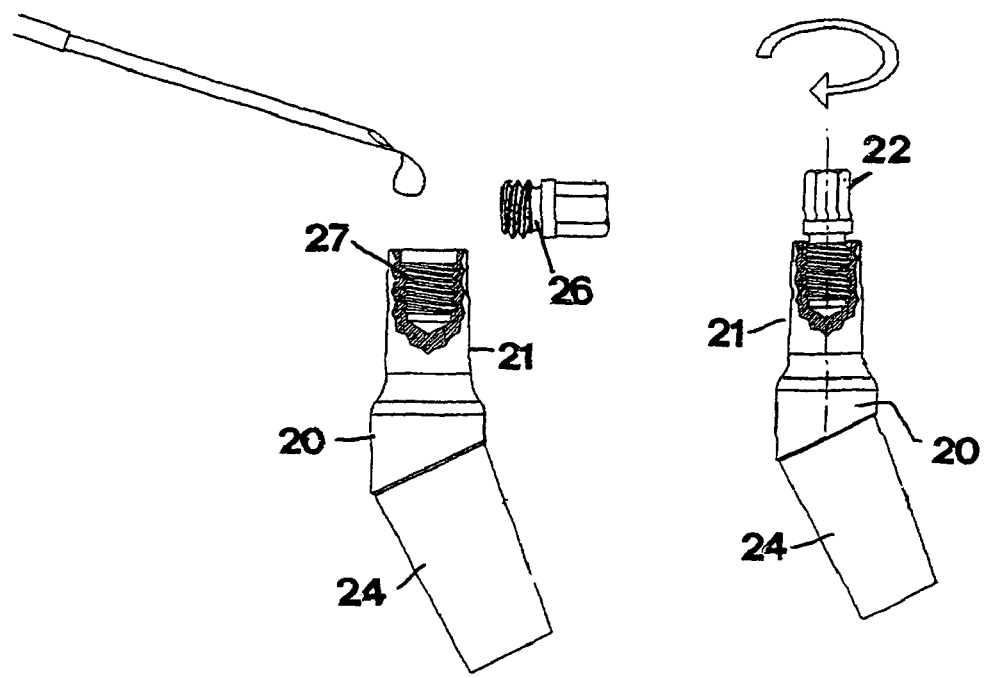
FIGS. 5 and 6 are schematic side views, in partial longitudinal section, of an abutment for dental implants according to a further embodiment in two assembling steps thereof.
Figure 10:
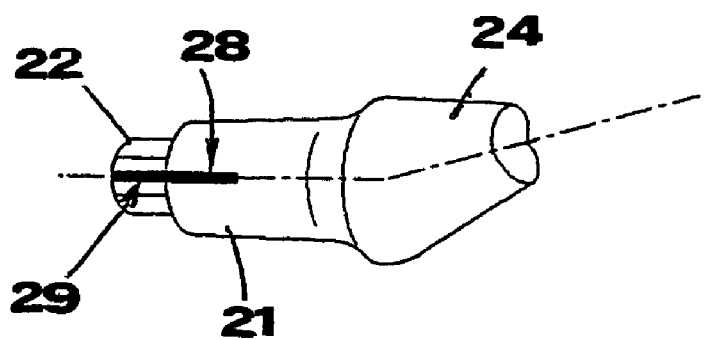
FIG. 10 is a further side view of the abutment of FIGS. 5 and 6, showing the positional references likewise the abutment shown in FIG. 3.
Figure 9:
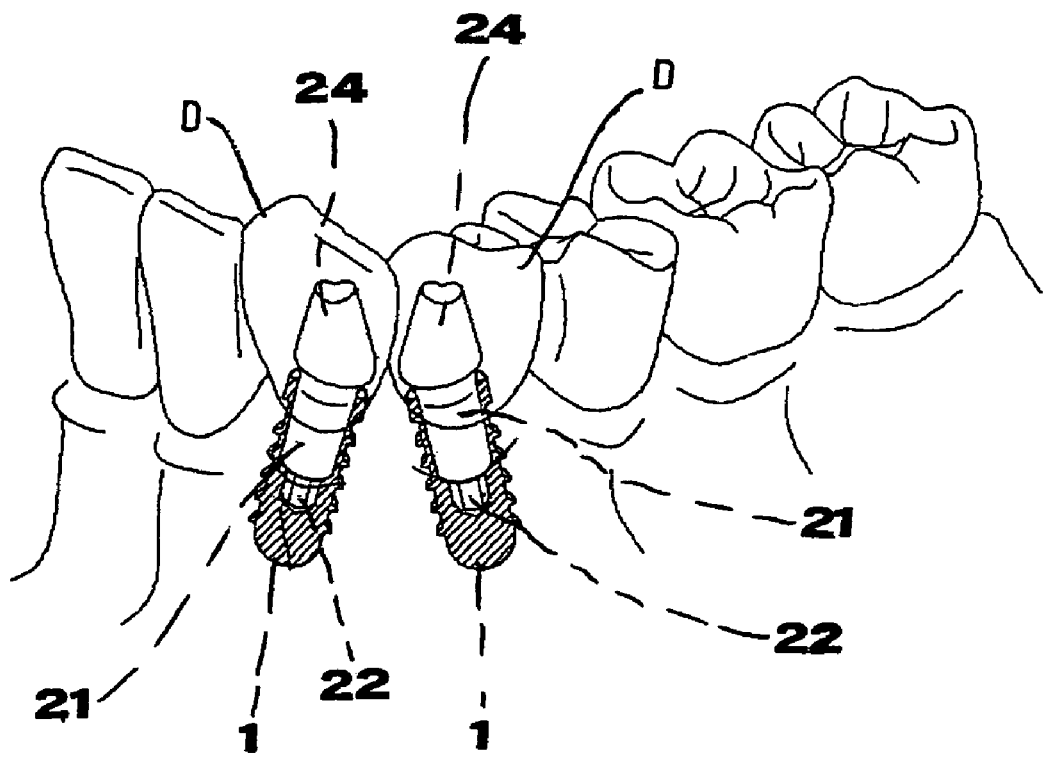
FIG. 9 is a schematic exploded view, partially in section, of a dental arch with an implant made by using the abutments shown in FIGS. 7 and 8.
Figure 11:
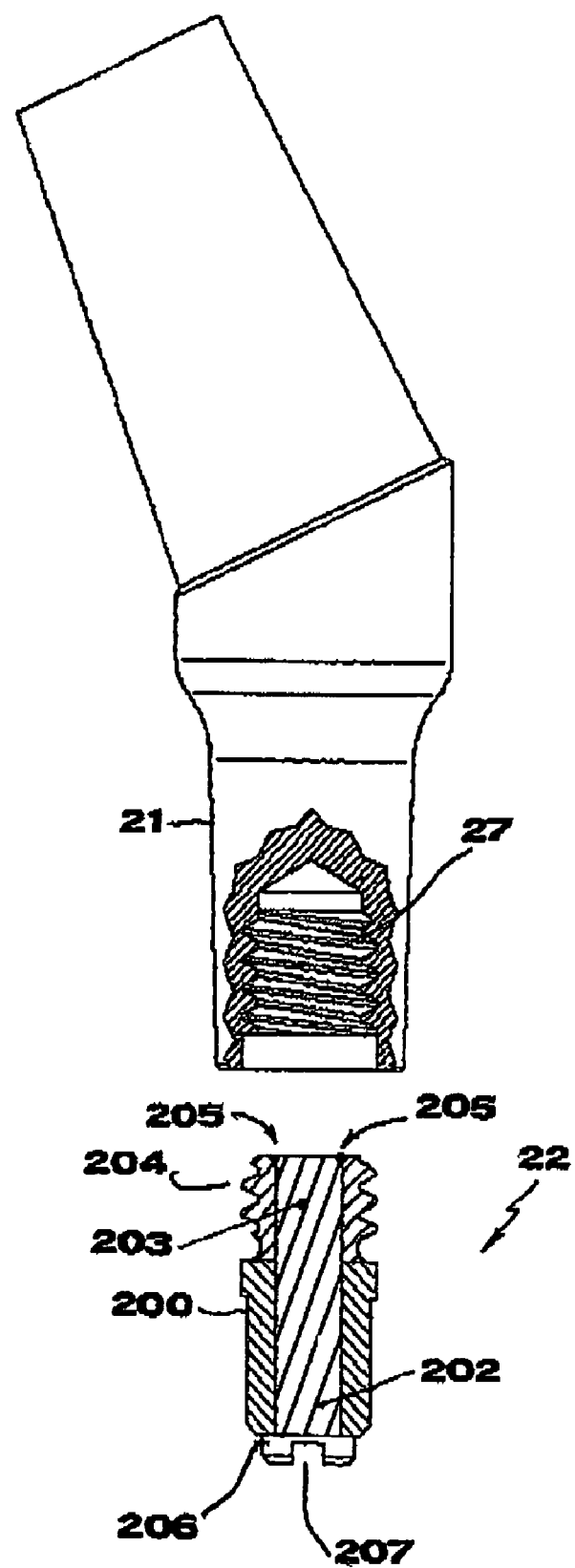
FIG. 11 is an exploded view in partial longitudinal section of a further embodiment of an abutment for dental implants according to the invention.
Figure 12:
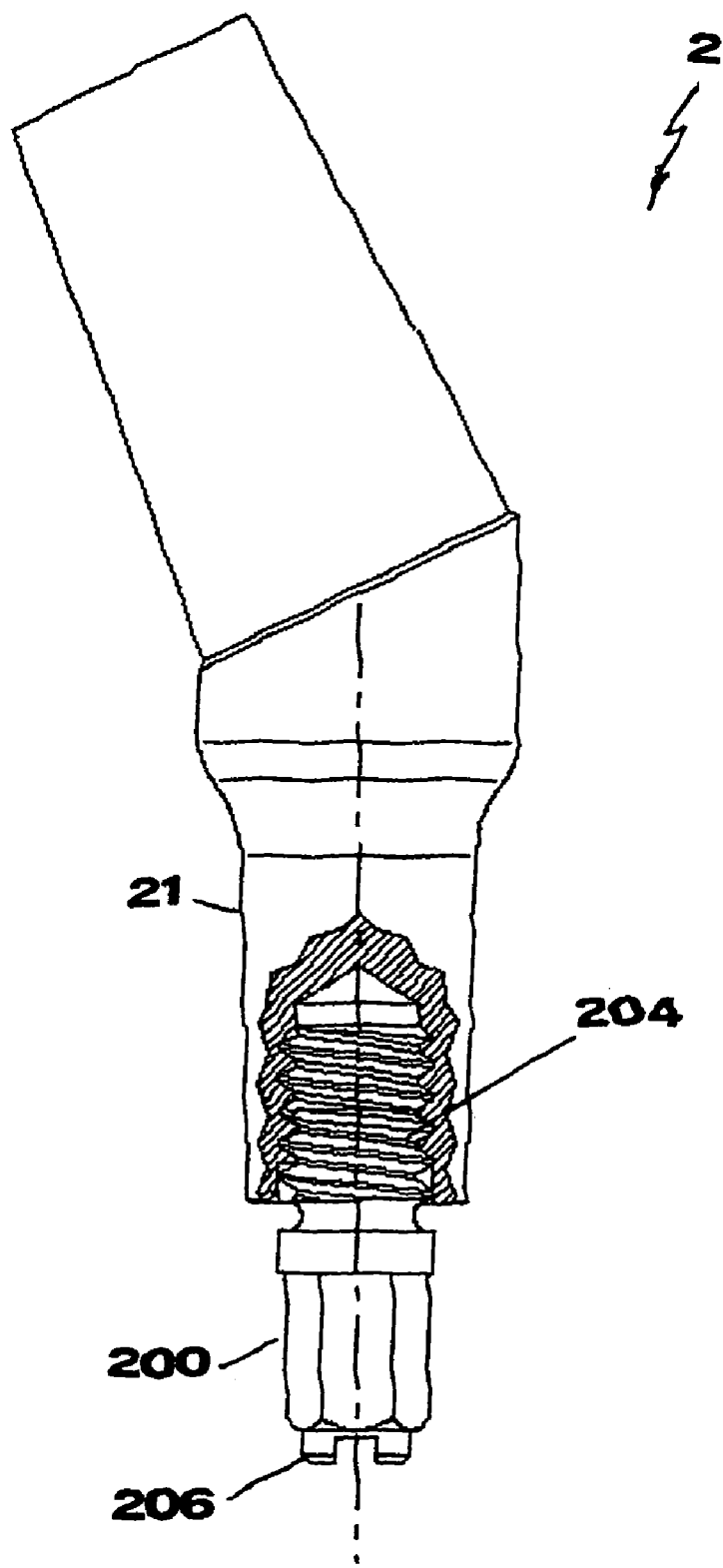
FIG. 12 shows the abutment of FIG. 11 in assembled condition.

Moreover, the coronal end (24) of the abutment (2) intended for the prosthesis (D) can be either in line with the shank (21)—such as in the examples of FIGS. 1 and 3—or also angled or inclined—as in the examples of FIGS. 6, 10 and 12.

The truncated-cone shank (21) of the abutment (2) is, in correspondence of its cross-section, of a diameter lower than the above-standing portion (20) to which it is connected without interruption by a radiused portion (23) with concave surface, the concavity of said surface facing outwardly. The said appendix having polygonal cross-section (22) is in apical position, that is, located below the shank (21) of the abutment (2); and the coronal part (20) of the latter is on the opposite side of the appendix (22) with respect to the shank (21). In practice, the appendix (22) is the lower end of shank (21).

Figure 15:
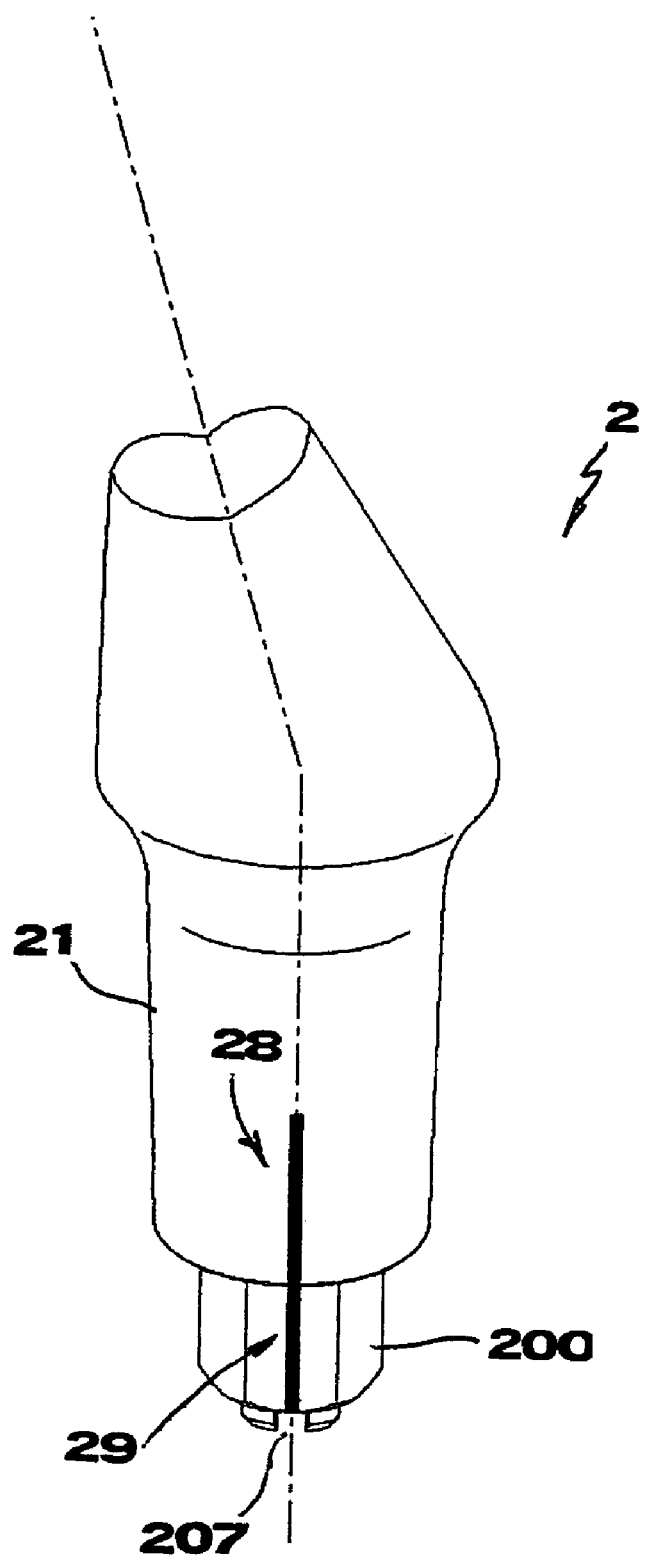
FIG. 15 is a schematic exploded view of the abutment of FIG. 11 and FIG. 12 after the milling of the part intended for the prosthesis, and the marking of the positional references.

The drawings show the shank 21 as being circular in cross-section, especially in FIGS. 10 and 15. FIGS. 7-9 and 13 also indicate that the shank 21 is circular. When a circular shank is fitted into a cavity it can be arranged in a plurality of rotational positions. There is no structure which prevents removing the shank, rotating it a finite amount, and then placing it back into the cavity. The circular shape of the shank permits the shank to be placed in the cavity in any rotational position between 0° and 360°. Conventional geometry allows the spacing between rotational positions to be infinitely small, and therefore the number of rotational positions between 0° and 360° is infinitely large. Therefore by the showing of a circular cross-section of the shank 21, an infinite number of rotational positions a possible for the shank 21 in the cavity 11.

The height (h) of said shank (21) may be chosen of a value greater than the useful height (h') of the cavity (11) formed in the fixture (1), so as to favour, in the condition of FIG. 3, the grow of the gingival tissue around the section between the upper base (110) of the fixture (1) and the lower part, that is, the part interested by the radiused portion 23 and by the portion 230 of the shank protruding outwardly of the fixture (1) of abutment (2). By the term useful height (h') it is meant the depth of penetration of the shank (21) thereinside.

The fixture (1) can be positioned either flush with the crest, that is, with the upper base (110) at the same level as the bony crest (30), or under the crest, that is, more deeply, depending on the choice operated by the doctor.

Figure 2A:
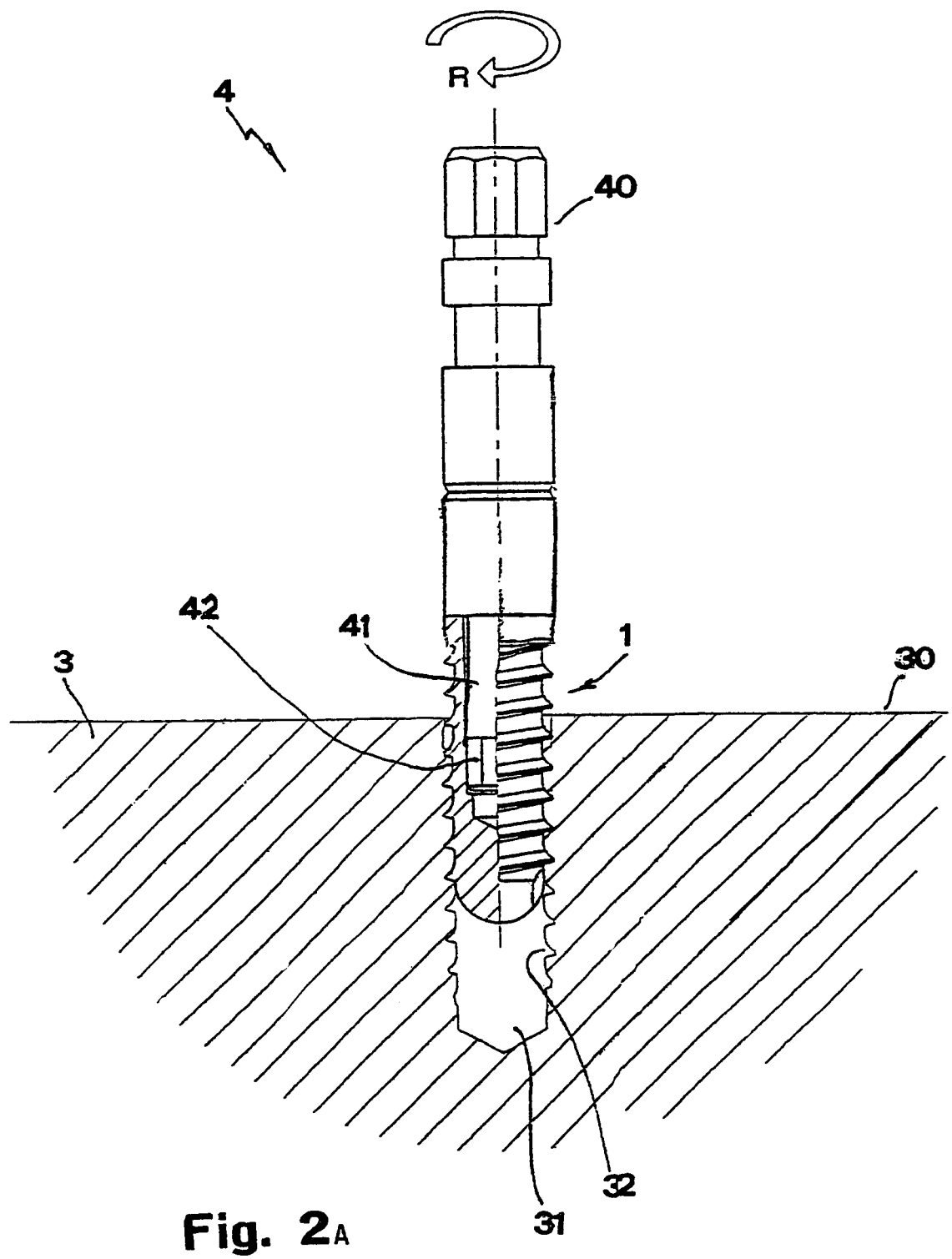
FIG. 2A shows schematically the positioning of a fixture in the implant's seat.
Figure 2B:
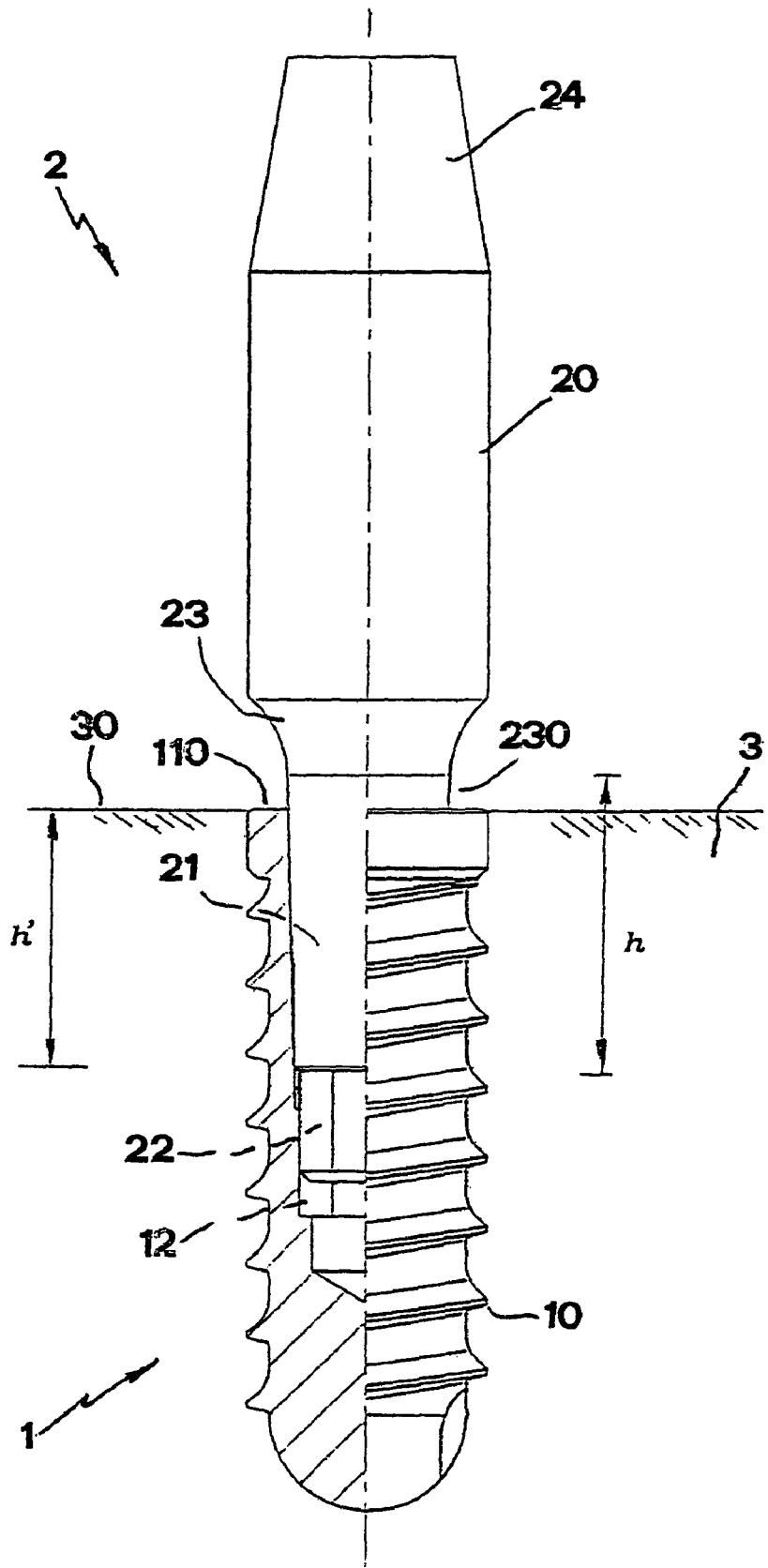
FIG. 2B shows schematically an abutment associated with the fixture within the implant's seat.

For the positioning of the fixture (1) at the predetermined point, the doctor—after having operated an osteotomy, that is, after having drilled a hole (31) in the bone (3) and, where necessary, formed a female threading (32) on the wall of the same hole, corresponding to the threading (10) of the fixture (1)—he/she can use the tool (4) illustrated in FIG. 2A. The said tool comprises a maneuvering upper portion (40) and, on the opposite side or below, a cylindrical shank (41) with a terminal appendix (42) having polygonal cross-section, that is, with a shape corresponding to the seat (12) of fixture (1). The diameter of said shank (41) is less that the maximum diameter of the cavity (11) formed in the fixture (1) (preferably equal to the minimum diameter of such cavity) to allow the positioning of the respective appendix (42) within the seat (12) of fixture (1) without interference between the tool's shank (41) and the inner wall of the cavity (11).

To position the fixture (1) at the desired level, the doctor places the portion (42) of tool (4) into the fixture's seat (12) and, by rotating the tool as indicated by the arrow (R) in FIG. 2A, screws the fixture down into the bone (3).

Once the fixture (1) has been positioned at the desired depth within the bony tissue (30), the doctor can fit the abutment (2) therein. To do so, he/she pushes the shank (21) of the abutment (2) into the cavity (11), with the polygonal appendix (22) of the abutment (2) into the seat (12) of fixture (1). The interference between the walls of said shank (21) and cavity (11) ensures a perfect hermetic seal and maximum stability in the fixture-abutment connection; and the positioning of said appendix (22) within said seat (12) ensures that no relative rotation will occur between the fixture (1) and the abutment (2) after said coupling.

Both said shank (21) and cavity (11) are Morse-tapered. As said before, there is interference between the walls of shank (21) and cavity (11), i.e. the shank (21) fits within cavity (11) and the external wall (210) of shank (21) mates the cavity wall (120) inside fixture (1). Since the abutment shank (21) and the cavity (11) provided inside the fixture (1) each have a Morse taper, a very tight fit of these parts relative to each other is provided, thus ensuring a perfect seal between them.

Moreover, since the abutment shank (21) and the cavity (11) each have a Morse taper, a friction fit is created between the external wall of shank (21) and interior wall of cavity (11), thus providing locking of abutment (2) to fixture (1) without making use of any passing screw or other type of external or auxiliary connection means. Self locking due to friction between Morse-tapered components is per se known.

In general, the abutment (2) is intended to be stably coupled with the fixture (1) subsequently to the osteo-integration of the latter.

Advantageously, according to the present invention, the said appendix having polygonal cross-section (22) is pivotally engaged to the remaining part (20, 21, 23, 24) of the abutment (2), so that the appendix (22) can rotate about its own longitudinal axis, with respect to the remaining part of the abutment (2) and, in particular, about the shank (21).

In practice, the lower end (22) of abutment (2) is rotatably connected to the shank (21) thereof. In other words, the appendix (22) is connected to shank (21) in such a way that rotation of the same appendix relative to the shank can occur.

For example, and reference being made to FIGS. 4, 5 and 6 of the attached drawings, the said appendix (22) is engaged to the shank (21) by means of a screw connection formed by a threading (27) formed on the outer surface of a stem (26) of the appendix (22) and a corresponding threading (27) formed on the inside surface of the shank (21), the latter being hollow to receive the threaded stem of the appendix (22). In other words, according to this exemplary embodiment of the invention, the appendix having polygonal cross-section (22) of the abutment (2) is screwed within the shank (21) thereof.

As shown in the drawings, appendix (22) and shank (21) are coaxial, i.e. they are aligned along the same longitudinal axis, so that appendix (22) can rotate about the longitudinal axis of shank (21).

Moreover, advantageously, in order to establish a positional reference between the appendix (22) and the shank (21) of the abutment (2), that is, to know all the time the mutual orientation of the appendix (22) and shank (21), provision is made for marking these two elements of the abutment, preferably by means of two indelible marks. For example, provision may be made, as shown in FIGS. 3 and 10, for marking by a laser two rectilinear segments (28, 29) on the terminal part of the shank (21) and respectively the appendix (22), the said segments being developed longitudinally to these two elements of the abutment. Alternatively, the said rectilinear segments (28, 29) may be formed by a milling or punching operation. It will be understood that in place of the marking of said segments (28, 29) provision may be made for any other means suitable for establishing a mutual position reference between the appendix (22) and the shank (21).

When, subsequently to the so-called "taper seating", that is, after the forcing of the shank (21) of abutment (2) into the fixture (1) and the consequent positioning of the abutment's appendix (22) within the corresponding impression (12) of the fixture (1), it is necessary to remove the abutment (2)—after having removed the prosthesis (D)—it is sufficient, by means of a forceps, to rotate the upper part (24) clockwise or anticlockwise by less of ¼ turn, this rotation being allowed by the screw connection between the shank (21) of abutment (2) and the appendix (22) which, contrary to the part supporting the prosthesis (D), does not rotate as it is inserted into the seat with polygonal cross-section (12) of the fixture (1)—see FIG. 16A. The said rotation, although of modest extent, is still sufficient to allow the "unseating" of the abutment, that is, the disconnection of the abutment's shank (21) from the seat (11) of the fixture (1), thereby eliminating the Morse-taper coupling made between these two elements of the implant. In other words, the appendix (22) can rotate relative to shank (21) within, i.e. inside, the impression (12) provided at bottom of cavity (11). At this point, it is sufficient that the doctor will exert a slight traction on the abutment already engage by the forceps to achieve the complete extraction of the abutment—see FIG. 16B. The appendix (22), however, remains linked to the shank (21). Experimental tests conducted by the applicant have allowed to verify that the torque to be applied for the unseating of the abutment is less than 50% of that necessary for unseating a conventional abutment with one-piece polygonal appendix (which is subjected also to a heavy risk of breaking due to stresses exceeding the limit of resistance to torsion), and that the tensile load to be exerted for the extraction of the abutment from the fixture is less than 5% of that required for the extraction of a conventional abutment. Consequently to this, the risk of damaging the bony structure in correspondence of the implant seat is greatly reduced, the load exerted by the doctor is also reduced, and the discomforts for the patient are less, also because of the shorter duration of the operation.

If the abutment is to be taper-seated again, the abutment's appendix (22) is rotated beforehand, to restore the alignment of the marks (28, 29), that is, the original orientation of the appendix (22) with respect to the shank (21).

Figure 7:
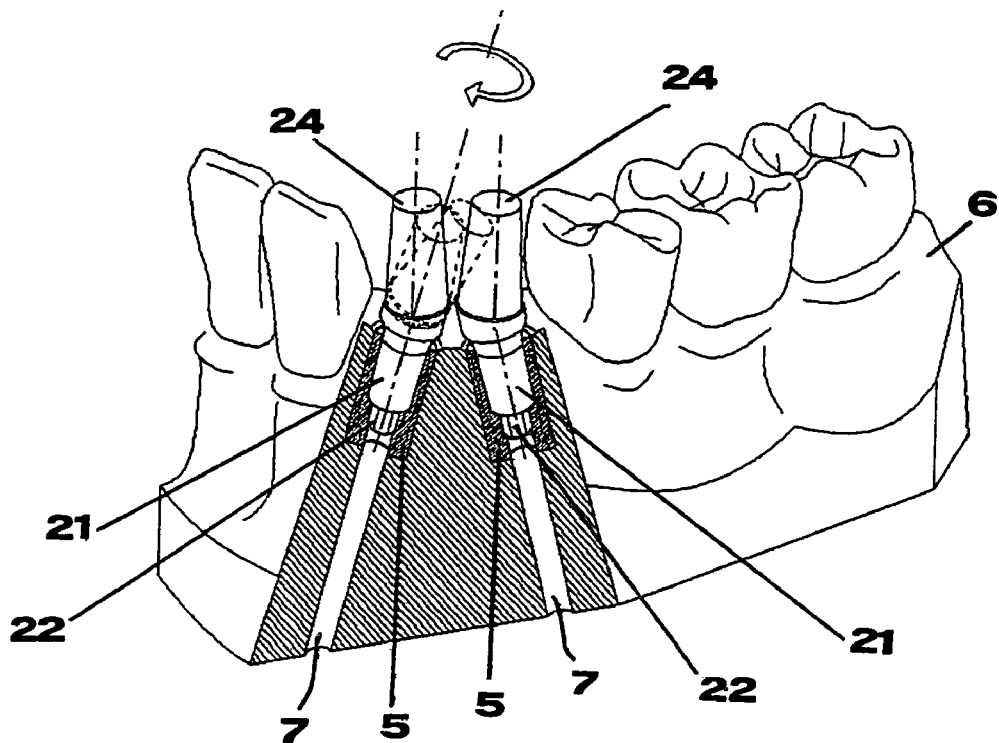
FIG. 7 is a schematic exploded view, partially in section, of a plaster cast of the implant's seat during the positioning of one abutment and with a second abutment already positioned.
Figure 8:
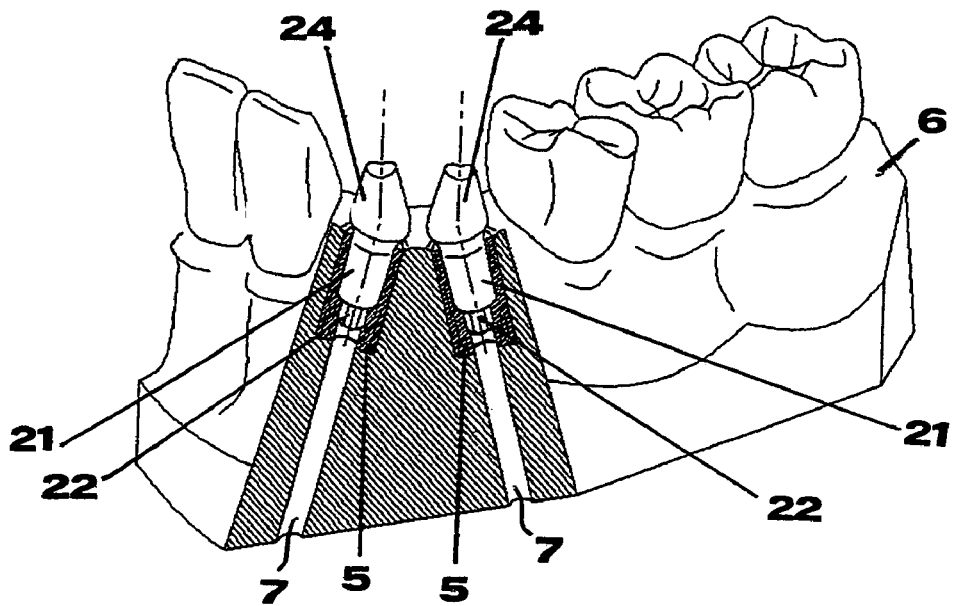
FIG. 8 shows, in a view similar to FIG. 7, the cast with both the abutments properly positioned into the respective fixtures.

An abutment for dental implants according to the invention can be supplied either pre-assembled, that is, with the appendix (22) already engaged to the shank (21), or into two non-assembled parts. In the first case, the said marking is factory-made after having screwed, but not all the way in, the appendix (22) into the shank (21). In the second case, the marking may be carried out by the doctor or the dental mechanic, as described later on with reference in particular to FIGS. 5-10 of the attached drawings:

in the first place, there is applied a small amount of impermanent, slow-setting glue on the base of the shank (21) and on the threaded stem of the appendix (22), as schematically shown in FIG. 5, thereby obtaining a temporary welding of these two abutment's elements in which the time the glue takes to set is sufficiently long to allow carrying out the operations below described: for the said glueing of the appendix (22) to the shank (21) use can be made of, for example, self-polimerizing composites and/or dental cements normally available on the market (for example, the monocomponent dental composite, code F3140-01, supplied by the same applicant);

afterwards, the appendix (22) is screwed, not all the way in, down into the abutment's shank (21), as illustrated in FIG. 6;

then the shank (21) of abutment (2) is positioned in a similar fixture (5) already disposed in the plaster cast (6) of the patient's dental arch in correspondence of the implant's seat in order, for example, to dispose the abutment's part (24) parallel to the corresponding part (24) of an abutment already positioned into the cast: the similar fixture (5)—which is known per se and also called "analogous" in jargon, reproduces internally the shape of the fixture (1), while externally is so shaped as to ensure a suitable retention within the plaster of the cast—is also obtainable from a material more economical than that used for making the fixture (1), and is open below to allow the removal of the abutment (2)—once the latter has been oriented as desired—with the aid of a pin (not shown) which is introduced into a corresponding hole-channel (7) formed in the same cast (FIG. 7);

following this, after a predetermined time necessary to make the glue set between the shank (21) and the appendix (22), the part (24) of the abutment (2) is milled (see FIGS. 8 and 10 where the said abutment's part 24 has a shape different from that exhibited by the same part 24 in FIG. 26) for receiving the prosthesis (D), then the abutment can be handed over to the doctor who will provide for its positioning within the fixture (1) already implanted in the patient.

Should, after having taper-seated the abutment (2), be necessary to extract the latter, it would be sufficient to perform the operation of unseating and extraction previously described, as the glue applied between the appendix (22) and the shank (21) of the abutment (2) causes only a weak retaining action between the parts and, accordingly, does not prevent the relative rotation of these two elements of the abutment when a torque is applied of an intensity sufficient to perform the unseating: in other words, and as resulting from tests carried out by the applicant, the resistant torque due to the glue which holds the said elements together, is far less than that necessary for obtaining the unseating of the abutment in the absence of glue, so that the action exerted by the doctor on the part (24) for the unseating is more than sufficient also to win the resistant action of the glue.

The fixture (1) and the abutment (2) can be made, for example, from a biocompatible material such as titanium of medical grade 5 (UNI 9673, ISO 5832), or from zirconium oxide ($ZrO_2$) or aluminum oxide ($Al_2O_3$).

Figure 13:
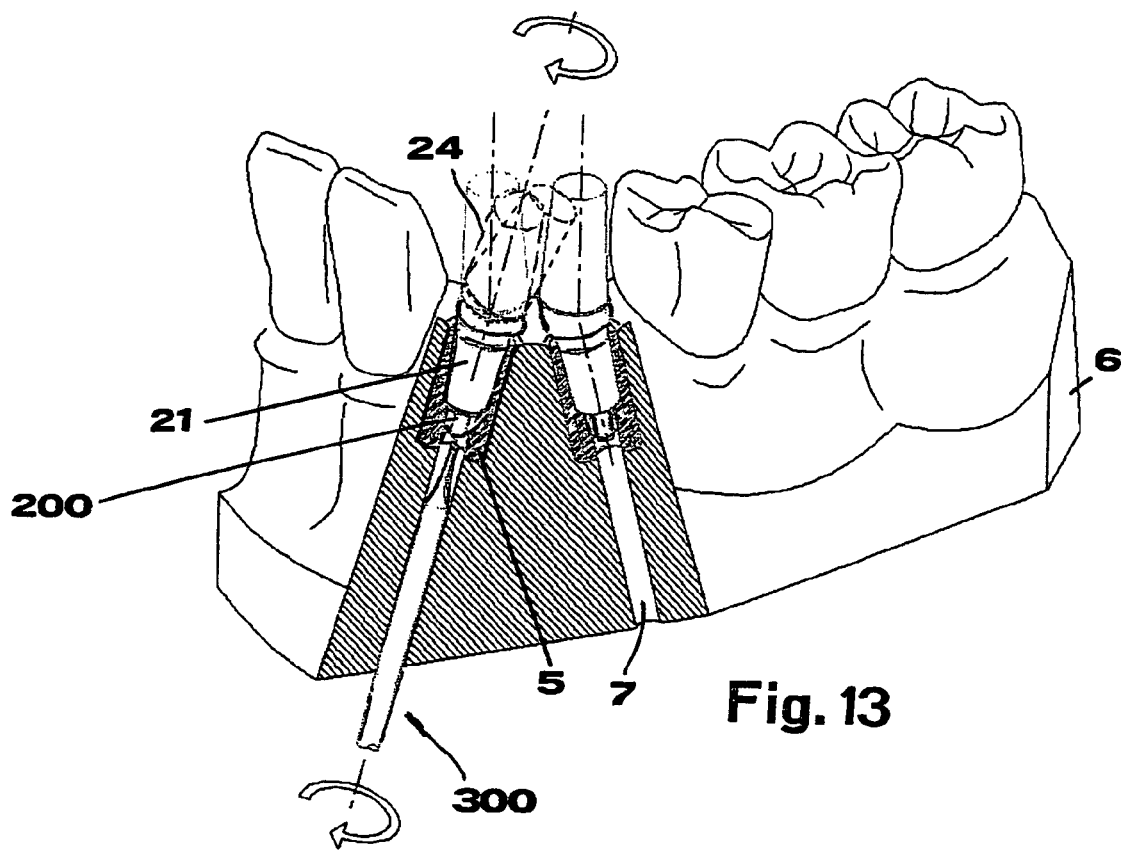
FIG. 13 shows schematically the positioning of the abutment of FIG. 12 in the plaster cast of a dental arch.
Figure 14:
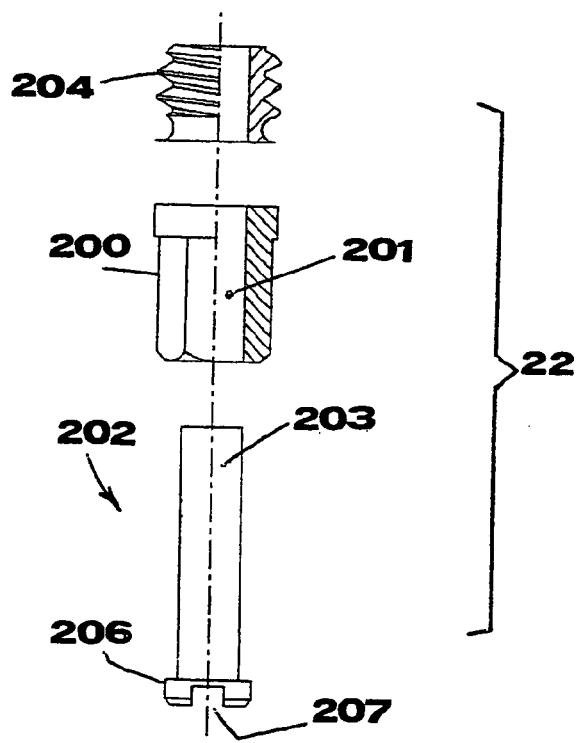
FIG. 14 is a schematic exploded view in partial longitudinal section of the appendix (22) of the abutment of FIG. 11 and FIG. 12.

According to the example illustrated in FIGS. 11-15 of the attached drawings, the said appendix (22) is in more elements (instead of in one-piece as in the example previously described), and comprises a body (200) of polygonal (hexagonal, for example) cross-section, with central through hole (201), a pivot (202) going through said hole (201) in such a way that a portion (203) of its stem protrudes from the body (200) over a predetermined length, and a bush (204) having external threading and fitted on the portion (203) of the pivot (202) protruding from the body (200) and fixed on the same pivot's portion (for example, by means of two laser welding spots 205): the head (206) of the said pivot (202) being on the side opposite to said portion (203) with respect to the body (200) and being provided with a diametral notch (207). As illustrated in the attached drawings, the said elements (200), (202) and (204) are coaxial to each other, and the threading of bush (204) is intended to engage the threading (27) of the abutment's shank (21). After positioning the abutment's shank (21) within the corresponding analogous (5) of the plaster cast (6), which reproduces the patient's dental arch, so as to orient the same abutment as desired by using a screwdriver tool (300) introduced in the relevant hole-channel (7) of the cast, as illustrated in FIG. 13, and by acting with the blade of the screw-driver on the notch (207) of the pivot's head (202), the appendix (22), that is, the assembly (200, 202, 204) is screwed down into the shank (21) as far as to block the same appendix to the latter and thereby fixing the mutual position of the appendix (22) and the abutment's shank (21) without using the glue. Afterwards, provision may be made for an anatomic milling of the abutment's part (24) intended for the prosthesis (D), and the marking of references (28) and (29).

Practically, the construction details may vary in any equivalent way as far as the shape, dimensions, elements disposition, nature of the used materials are concerned, without nevertheless departing from the scope of the adopted solution idea and, thereby, remaining within the limits of the protection granted to the present patent.

What is claimed is:

1. A dental implant comprising: a fixture defining a tapered cavity at an open end of said fixture, said fixture also defining a polygonal seat arranged at an end of said cavity diametrically opposite said open end; an angular abutment with a tapered shank and a prosthesis connection arranged on one end of said shank, said abutment also including an appendix arranged on another end of said shank diametrically opposite said prosthesis connection, said appendix having a shape complementary to a shape of said polygonal seat, said tapered cavity and said tapered shank being shaped to have said shank fit inside said cavity, a taper of said shank and of said cavity being arranged to cause said shank to lock into said cavity when said shank is fitted in said cavity, said appendix being rotatably connected to said shank; an alignment arrangement on said appendix and said shank, said alignment arrangement providing a mutual orientation of the appendix and the shank.

2. A dental implant in accordance with claim 1, wherein: said appendix is rotatably connected to said shank about a longitudinal axis of said appendix.

3. A dental implant in accordance with claim 2, wherein: said shank is positionable in said cavity in an infinite number of rotational positions about said longitudinal axis.

4. A dental implant in accordance with claim 1, wherein: said shank is positionable in said cavity in an infinite number of rotational positions.

5. A dental implant in accordance with claim 1, further comprising:
a screw connection connecting said appendix to said shank.

6. A dental implant in accordance with claim 1, wherein: said alignment arrangement include indicia to indicate an orientation of said appendix relative to said shank.

7. A dental implant in accordance with claim 1, wherein: said appendix includes a body with a polygonal cross-section defining a through hole, said appendix including a pivot arranged in said through hole with a stem portion of said pivot extending from said body over a predetermined length, said appendix including a bush having external threading, said bush being arranged on said stem portion of said pivot, said pivot including a head arranged on a side of said pivot opposite to said stem portion with respect to said body, said head including a maneuvering portion engageable by a tool.

8. A dental implant in accordance with claim 1, wherein: a half angle of said tapered shank and said tapered cavity has a nominal value of 1.5°.

9. A dental implant in accordance with claim 1, wherein: said taper of said cavity and shank are arranged to cause said cavity and said shank to friction lock together when said shank is inserted into said cavity.

10. A dental implant comprising: an angular abutment and a fixture, said abutment including a Morse-tapered truncated cone shank to be fitted into a corresponding Morse-tapered cavity defined by said fixture, a taper of said cone shank and a taper of said cavity forming a self-locking connection between said abutment and said fixture; said abutment including an appendix having a polygonal cross-section rotatably arranged below said shank; a bottom of said cavity of said fixture defining an impression corresponding to said appendix, said abutment and said fixture being arranged to have said appendix be fitted into said impression; said abutment being also provided, on the side opposite to said appendix with respect to said shank, with a portion intended for supporting a dental prosthesis, wherein said shank of the abutment can be rotated about a longitudinal axis of said shank, relative to said appendix and said tapered cavity when said appendix is within said impression provided in said bottom of said cavity of said fixture; an alignment arrangement on said appendix and said shank, said alignment arrangement providing a mutual orientation of the appendix and the shank.

11. The dental implant of claim 10, wherein said appendix of the abutment is engaged to said shank by a screw connection.

12. The dental implant of claim 10, wherein said appendix of the abutment is screwed within said shank.

13. The dental implant of claim 10, wherein said alignment arrangement comprise marks.

14. The dental implant of claim 13, wherein said marks are indelible.

15. The dental implant of claim 13, wherein said marks include two straight segments longitudinally oriented with respect to the shank and the appendix of the abutment.

16. The dental implant of claim 13, wherein said marks are produced by a laser or by milling or punching.

17. The dental implant of claim 10, wherein a preset amount of glue is applied between said appendix and said shank of the abutment.

18. The dental implant of claim 10, wherein said appendix is provided, on the side opposite to said shank, with a seat for a corresponding tool.

19. The dental implant of claim 10, wherein said appendix is made up of a plurality of elements.

20. The dental implant of claim 19, wherein said appendix is made up of three elements coaxial to each other.

21. The dental implant of claim 20, wherein said appendix comprises a body with polygonal cross-section with a central through hole, a pivot going through said hole in such a way that a portion of said pivot protrudes from the body over a predetermined length, said appendix including a bush having external threading, said bush being fitted and fixed on the portion of the pivot protruding from the body, said pivot including a head being on a side of said pivot opposite to said portion with respect to the body and provided with a maneuvering portion which can be engaged by a tool.

22. A dental implant comprising: a fixture adapted to be implanted in a jaw of a user, said fixture having an open end defining an opening, said fixture defining a tapered cavity extending inward from said opening, said fixture also defining a polygonal seat arranged at an end of said cavity diametrically opposite said open end; an angular abutment including a tapered shank, said tapered shank being shaped to fit inside said tapered cavity, said abutment including a prosthesis connection arranged on one end of said tapered shank, said abutment also including an appendix arranged on another end of said tapered shank diametrically opposite said prosthesis connection, said appendix having a shape complementary to a shape of said polygonal seat, a taper of said shank and of said cavity being arranged to cause said shank to lock into said cavity when said shank is fitted in said cavity, said appendix being rotatably connected to said shank; an alignment arrangement on said appendix and said shank, said alignment arrangement providing a mutual orientation of the appendix and the shank.

* * * * *